(12) United States Patent
Voorhees et al.

(10) Patent No.: US 7,044,960 B2
(45) Date of Patent: May 16, 2006

(54) METHOD AND APPARATUS FOR PROVIDING NON-INVASIVE ULTRASOUND HEATING OF THE PREOPTIC ANTERIOR HYPOTHALAMUS

(75) Inventors: Marc E. Voorhees, Arvada, CO (US); Gary A. Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 184 days.

(21) Appl. No.: 10/666,902

(22) Filed: Sep. 17, 2003

(65) Prior Publication Data

US 2005/0060012 A1 Mar. 17, 2005

(51) Int. Cl.
*A61F 7/00* (2006.01)
*A61B 18/04* (2006.01)

(52) U.S. Cl. .............................. 607/96; 606/27; 606/28
(58) Field of Classification Search ................. 607/96; 606/27–31; 601/2
See application file for complete search history.

(56) References Cited

U.S. PATENT DOCUMENTS

| | | | | |
|---|---|---|---|---|
| 4,662,383 | A | 5/1987 | Sogawa et al. | 128/784 |
| 4,865,047 | A | 9/1989 | Chou et al. | 128/784 |
| 6,090,132 | A | 7/2000 | Fox | 607/96 |
| 6,156,057 | A | 12/2000 | Fox | 607/96 |
| 6,188,930 | B1 | 2/2001 | Carson | 607/101 |
| 6,375,674 | B1 | 4/2002 | Carson | 607/104 |
| 6,461,379 | B1 | 10/2002 | Carson et al. | 607/104 |

FOREIGN PATENT DOCUMENTS

WO    WO 99/07314    8/1998

OTHER PUBLICATIONS

Dr. Malcolm C. Brown; "Ultrasound Diathermy Apparatus"; Medical Dictionary 2000 (1 Page).
Kullervo Hynynen; "Focused Ultrasound Surgery Guided by MRI"; Sep./Oct. 1996—vol. 3, No. 5, Copyright (C) 1996 by Science & Medicine, Inc. (15 Pages).
Ajit Mal, Feng Feng, Michael Kabo, Jeffrey Wang; "Interaction of High Intensity Focused Ultrasound with Biological Materials"; SPIE'S NDE and Smart Structures Symp., Paper 4702-40, San Diego, CA, Mar. 2002 SPIE Copyright (C) 2002 (9 Pages).

(Continued)

*Primary Examiner*—Roy D. Gibson
(74) *Attorney, Agent, or Firm*—Marsh Fischmann & Breyfogle LLP (57) ABSTRACT

A method and system is provided to induce mild hypothermia in a patient through controlled heating of the preoptic anterior hypothalamus (POAH) in conjunction with cooling of patient's body. The system employs an ultrasound transducer that may be positioned extracorporeally to a patient skull for emitting ultrasound energy to the POAH. The ultrasound energy heats the POAH to inhibit thermoregulatory responses of the body such that a cooling means may more effectively cool bodily tissue in order to reduce a patient's core body temperature. Feedback sensors may be positioned at various locations on the patient in order to monitor the patient's core body temperature. A control apparatus included with the system controls the amount of heat the POAH receives and the amount of cooling the body receives based on the feedback signals from the sensors.

44 Claims, 9 Drawing Sheets

OTHER PUBLICATIONS

Zweifler, Alday, Voorhees, Carson; "A Novel Method to Induce Mild Hypothermia Via Surface Cooling"; American Academy of Neurology 2000; May 5, 2000.

Trembly, Hoopes, Moodie, Carson, Voorhees, Boulant; "Hypothalamus Warming for Ischemia Protection"; Proceedings of the International Symposium on Biomedical Optics; Jan. 20, 2001.

Ter Haar; "High Intensity Focused Ultrasound for the Treatment of Tumors"; Echcardiography; vol. 18, No. 4, 2001.

Kirkham, Padayachee, Parsons, Seargeant, House, Gosling; "Transcranial Measurement of Blood Velocities in the Basal Cerebral Arteries Using Pulsed Doppler Ultrasound: Velocity as an Index of Flow"; Ultrasound in Med. & Biol, vol. 12, No. 1, 1986.

Clement, Hynynen; "A Non-Invasive Method for Focusing Ultrasound Through the Human Skull"; Physics in Medicine and Biolog, vol. 47, 2002.

Clement, Hynynen; "Correlation of Ultrasound Phase with Physical Skull Properties"; Ultrasound in Med. & Biol., vol. 28, No. 5, 2002.

Aubry, Tanter, Pernot, Thomas, Fink; "Experimental Demonstration of Noninvasive Transskull Adaptive Focusing Based on Prior Computed Tomography Scans"; J. Acoust. Soc. Am. 113, Jan., 2003.

METHOD AND APPARATUS FOR PROVIDING NON-INVASIVE ULTRASOUND HEATING OF THE PREOPTIC ANTERIOR HYPOTHALAMUS

FIELD OF THE INVENTION

The invention relates to a method and system for inducing mild hypothermia in a patient. More particularly, the invention relates to inducing mild hypothermia through non-invasive heating of the preoptic anterior hypothalamus (POAH) in combination with cooling one or more portions of a patient's body.

BACKGROUND OF THE INVENTION

Stroke is one of the leading causes of death in adults and also a major cause of neurological disability. Until recently, stroke has been viewed as an untreatable event and all physicians could offer a stroke victim was rehabilitation to try to regain lost functions. In an effort to reduce the damage caused by strokes, a number of treatments have been proposed. In one interventional approach, known as neuroprotectant therapy, the intent is to limit the amount of neurological damage that occurs after the initial event. Neuroprotectant approaches includes the administration of several pharmacological agents and a treatment known as mild hypothermia, or a lowering of core body temperature by 2–4 degrees Celsius. The induction of mild hypothermia has been shown to inhibit several points of the chemical cascade that cause secondary cellular death after an ischemic event and to provide broad neuroprotection. Neuroprotectant therapy has also been applied to inhibit the effects of cardiac arrest as well as head trauma.

One method of inducing mild hypothermia is through heating of the preoptic anterior hypothalamus (POAH) that is located in the lower portion of the brain adjacent to the skull. It is known that the POAH is the thermostat for sensing core body temperature and controlling thermoregulatory responses in animals. The cooling mechanisms elicited by the POAH include reduction of metabolic energy generation, vasodilatation enhancing skin cooling, and sweating. Full vasodilatation can increase the rate of heat transfer to the skin as much as eight fold. An additional one degree Celsius increase in body temperature can increase sweating enough to remove ten times the basal rate of heat protection.

SUMMARY OF THE INVENTION

In conjunction with the present invention, it has been recognized that ultrasound energy may be utilized to heat the POAH in order to induce mild hypothermia in a patient. For example, such ultrasound energy may be emitted through one or more transcranial windows in order to extracorporeally heat the POAH. Such transcranial windows may include thin portions of the skull as well as openings within the skull. As will be appreciated, by focusing ultrasound energy of a predetermined frequency range and magnitude (i.e., power) on the POAH, thermoregulatory responses (e.g., shivering and/or vasoconstriction) of the patient may be overcome thereby facilitating the use of external cooling to a reduce a patient's core body temperature.

According to a first aspect of the present invention, a method for inducing mild hypothermia within a patient is provided wherein ultrasound heating of the POAH is combined with artificial cooling of a patient's body to enhance the rate at which such hypothermia is induced. In this regard, the method includes positioning a source of ultrasound energy relative to a patient's skull and applying ultrasound energy to the POAH to affect thermoregulatory responses of the body. In conjunction with application of the ultrasound energy to the POAH, one or more portions of the patient's body is cooled using an artificial cooling means in order to remove body heat. The combination of POAH heating with artificial cooling allows a patient's core body temperature to be rapidly lowered.

Artificial cooling may be performed externally to the body, internally to the body or utilizing a combination of external and internal methods. That is, artificial cooling may be intracorporeal and/or extracorporeal. For example, intracorporeal cooling may include endovascular cooling and/or cooling of the peritoneum. In this regard, cold saline solutions may be introduced into the patient's veins and/or into the abdominal cavity of the patient. As will be appreciated, such intracorporeal cooling is typically an invasive procedure, which may not desirable in all instances. Accordingly, external cooling may be performed instead of or in conjunction with such intracorporeal cooling.

When artificial cooling is performed externally, a number of cooling methodologies may be utilized. For example, external surfaces of the body may be cooled through the application of cold packs, ice blankets, and/or blowing gases (e.g., air) across a patient's skin (e.g., in conjunction with wetting of the skin). One cooling method utilizes one or more cooling pads that allow a thermal transfer fluid to circulate relative to a patient's body in order to conductively and/or convectively remove heat therefrom. Such cooling pads may generally be referred to as contact cooling means. These pads may further utilize fluid circulating pumps and/or temperature regulating systems (e.g., heat exchangers) for controllably adjusting the temperature of such fluid. Typically, fluids utilized with such pads will have a thermal coefficient that allows heat to be effectively transferred away from the patient. In this regard, liquids are generally utilized.

The cooling pads may allow for direct fluid contact with a patient's skin. That is, these cooling pads may comprise a membrane that fits on/over a portion of the patient's body such that fluid may circulate in a space between the membrane and a patient's skin. In this regard, a combination of convective and conductive heat transfer may be utilized to remove heat from the patient's skin. To prevent leakage from such membranes, fluids may be circulated under a negative pressure. In this regard, the negative pressure may allow the edges of the membrane to form a better seal with a patient's skin to prevent fluid leaks. Alternatively, such pads may be closed systems wherein one or more channels pass through the pad, that allow fluids to be circulated therethrough. In this regard, thermal energy may be exchanged with a patient through conductive contact with the pad. To enhance this conductive contact, the pad may be adhered directly to the patient's skin and/or utilize a gel, ointment or other medium to enhance heat transfer between the pad and the patient's skin. In one embodiment, the pad includes an adherent surface provided by a thermally conductive hydrogel layer juxtaposed to a fluid circulation layer. As with the membrane type cooling pads, fluids may be circulated through such closed system pads under negative pressure to provide enhanced circulation. When negative circulation pressures are utilized, the cooling pads (i.e., closed system and membrane type) may require internal structure(s) to maintain an adequate fluid flow path.

In one embodiment, that may be particularly apt for use with stroke patients, artificial cooling may be provided to a patient's head. This localized cooling allows a patient's brain tissue to be more effectively cooled in order to limit chemical cascades that can cause secondary cellular death after an ischemic event. As will be appreciated, heating of the POAH will result in conductive heating of adjacent tissue. In this regard, localized cooling of the patient's head may reduce or eliminate temperature increases of the adjacent tissue. However, it will be appreciated that cooling pads may be located on other regions of the body as well (e.g., on the patient's back, chest, thigh, etc.). Likewise, a plurality of pads may be utilized to increase the rate of heat exchange (e.g., heat removal) with a patient's body.

According to a second aspect of the present invention, ultrasound energy is utilized to non-invasively heat the POAH in order to induce mild hypothermia in a patient. The method includes positioning a source of ultrasound energy relative to a patient's skull and focusing ultrasound energy on a tissue region therein. This tissue region will at least partially coincide with the POAH. A predetermined amount of ultrasound energy may be applied to the tissue region to increase the temperature of the POAH. For example, sufficient ultrasound energy may be provided to raise the temperature of the POAH between about 0.5° Celsius and about 4° Celsius. The temperature increase may be monitored through secondary physiological responses (e.g., by monitoring core body temperature and/or skin conductivity). In any case, heating of the POAH will typically allow the patient's body to vasodilate and/or sweat, each of which act to lower the body temperature of the patient.

In one application, the entire POAH is heated (e.g., evenly heated) in order to better control the induction of hypothermia within a patient. In this regard, the ultrasound energy may be focused on a tissue region that substantially encompasses the POAH. However, this is not a requirement. What is important is that sufficient ultrasound energy is provided to a region within the skull to elevate the temperature of the POAH. In this regard, it is believed that applying ultrasound energy having a power in a range of between about 0.05 W and about 100 W is sufficient to controllably elevate the temperature of the POAH. More preferably, the power may be in a range of about 0.1 W to about 10 W. To effectively heat a tissue region coinciding with the POAH, it is believed that an intensity of between about 2.0 W/cm$^2$ and about 100 W/cm$^2$ may be utilized. As will be appreciated, the intensity of the ultrasound energy may depend upon the source area of an ultrasound transducer, focusing system for the transducer, and/or the power of the ultrasound energy. Furthermore, the power of the ultrasound energy may depend on the frequency and/or pulse length of an ultrasound device supplying the energy. In this regard, the frequency of the ultrasound energy may be varied between about 0.5 MHz and about 10 MHz while the pulse length may vary from a pico second (μs) range to continuous application. In any case, the frequency, source area and pulse length of an ultrasound source may each be selected to allow the resulting power and/or intensity of the ultrasound energy to be within the desired ranges.

The ultrasound energy may originate from any source acceptable for heating purposes so long as that source may be focused on a tissue region within a patient's skull. In this regard, the ability to focus ultrasound energy on a particular tissue region may prevent undue heating of overlying tissue (i.e., brain tissue) in which a reduced temperature may be desired. That is, focusing the ultrasound energy on the POAH allows for raising the temperature of the POAH while the temperature of the remainder of the patient's brain tissue may reduced for therapeutic purposes. Sources of ultrasound that may be utilized include, without limitation, imaging/diagnostic, medical, therapeutic and surgical ultrasound systems.

Ultrasound energy may be applied from any location that allows such energy to focus on the POAH. Furthermore, this energy may be applied in a non-invasive manner. For example, in one arrangement a source of ultrasound energy may be disposed externally relative to the patient's skull in order to heat the POAH. In this regard, the step of positioning may include positioning the source (e.g., a transducer) relative to one or more transcranial windows that allow ultrasound energy to be focused on the POAH. When positioned relative to such transcranial windows, a significant portion of ultrasound energy from a source is able to pass through the patient skull for POAH heating purposes. Such windows may include a transocipital window, a transtemporal window and a transorbital window. In another arrangement, an ultrasound transducer may be disposed within the patient body (e.g., within a nasal cavity) for heating purposes.

In order to focus the source of ultrasound on the POAH, one or more diagnostic visualization procedures may be utilized. For example, ultrasound imaging may be performed to identify the POAH within the patient's skull such that an ultrasound source (e.g., transducer) that will be utilized to heat the POAH may be properly focused. Alternatively, magnetic reasoning imaging (MRI) or x-ray may be utilized for POAH identification and transducer focusing.

According to another aspect of the present invention, a system is provided for inducing mild hypothermia within a patient. The system includes a source of ultrasound energy operable to focus energy on a tissue region within a patient's skull that at least partially coincides with or encompasses the POAH. The system further includes at least one sensor positionable on the patient's body to provide feedback signals indicative of a patient's body temperature (e.g., a core body temperature sensor, or a skin conductivity sensor). A controller regulates the amount of energy applied to the POAH by the source in relation the feedback signals received from the sensor(s). The system may further include a body cooling system for artificially cooling one or more portions of a patient's body. The cooling system may also be operatively interconnected to the controller. In this regard, cooling provided by the cooling system may also be regulated in relation to a patient's body temperature.

The cooling system may allow for internal and/or cooling to external portions of a patient's body. In one embodiment, a contact cooling means provides external cooling of the patient's body. Such an external cooling means will typically include a cooling pad for contacting a patient's body, a thermal exchange fluid, a fluid reservoir, a temperature regulating system (e.g., a heat exchanger) for controllably adjusting the temperature of the fluid, and a pump for circulating fluid through the cooling pad. As will be appreciated, variations may exist in each of the above noted cooling system components. For example, the fluid may circulate in a system utilizing multiple reservoirs or utilizing no reservoir. What is important is that one or more cooling pads is available for placement on a patient's tissue to enhance reduction of a patient's core body temperature.

The sensors utilized with the system may be any sensor operable to provide feedback signals indicative of the patient's body temperature. Such sensors may include, without limitation, core body temperature sensors and/or skin conductivity sensors. In the case of a core body temperature sensor, such a sensor may be attachable to one of the tympanic membrane, the esophageal and the nasopharyngeal.

DETAILED DESCRIPTION

Figure 1:
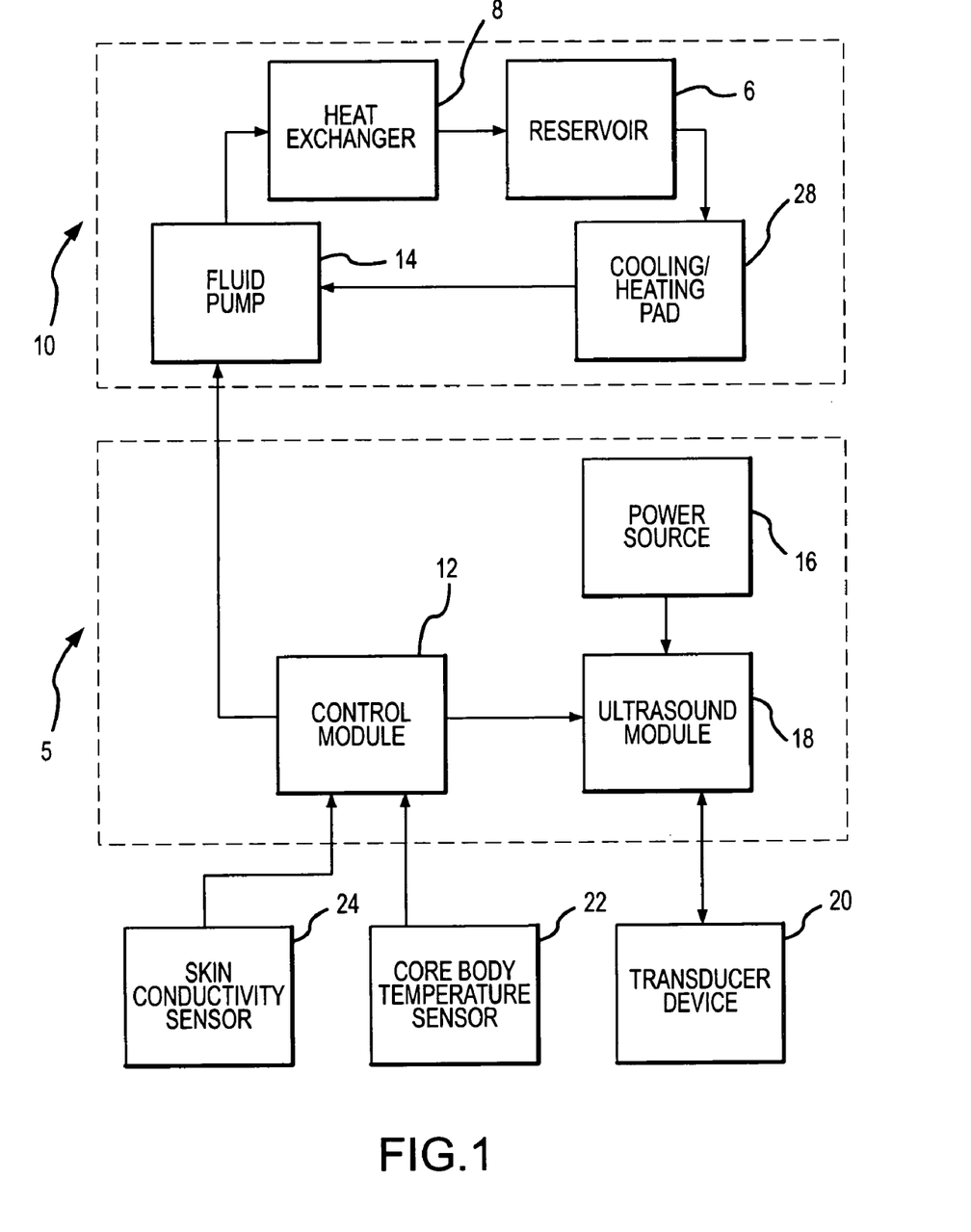
FIG. 1 discloses a diagram for the heating system described herein.

Disclosed in FIG. 1 is a diagram for one embodiment of the POAH heating and body cooling system described herein. One application of the system is the heating of the preoptic anterior hypothalamus (POAH) through the exposure of the POAH to a source of ultrasound energy, which may be located extracorporeally to a patient's skull. In this regard, the POAH may be heated in a non-invasive procedure in order to induce mild hypothermia in a patient receiving such treatment. The PAOH heating system 5 includes an ultrasound module 18 that produces and analyzes electrical signals and an interconnected transducer device 20 for positioning relative to a patient's skull. The transducer device 20, which may include an array of transducers, converts the electrical signals from the ultrasound module 18 into ultrasound energy. The transducer device 20 may also convert ultrasound echoes into electrical signals. In any case, the ultrasound energy may be focused on the POAH for heating purposes. The detailed configuration of the PAOH heating system 5 will be described in greater detail below.

In connection with the ultrasound module 18 is a control module 12. The control module includes programming for directing the output of the ultrasound module in response to various external inputs. This control module 12 may comprise any number of electronic devices (such as a personal computer) that provide automatic monitoring and control functions. This control module 12 includes the necessary computational power to measure incoming control signals and in response provide command signals for directing the operations of external components.

In the PAOH heating system 5 disclosed in FIG. 1, feedback signals are provided to the control module 12 through a skin conductivity sensor 24 and/or a core body temperature sensor 22. The skin conductivity sensor 24 may include a number of electrodes that may be positioned on various locations of the skin. As the amount of liquid (such as sweat) accumulates on the skin surface, the conductivity of the skin will increase. Such conductivity sensors are well know and commercially available.

Also connected to the control module 12 is the core body temperature sensor 22. This temperature sensor may be attached to a number of body parts that are known to provide an accurate indication of core body temperature. These locations may include the tympanic membrane, esophageal, or nasopharyngeal regions. The sensor generates an electric signal whose magnitude is indicative of the temperature measured. Such temperature sensors are known to one skilled in the art and are commercially available.

Also attached to the control module 12 is a body cooling system 10. As will be described in greater detail below, the body cooling system 10 includes one or more external cooling/heating pad(s) 28 for application to a patient that is operative to cool/heat a patient via thermal exchange. This pad 28 is fluidly interconnected to a fluid pump 14, which circulates a temperature-regulated fluid through the pad 28. The fluid pump 14 is fluidly connected to a fluid reservoir 6 and a temperature regulation system or heat exchanger 8. As will be appreciated, incorporation of such pads 28 may increase the rate at which hypothermia may be induced in a patient or otherwise provide enhanced control of the overall cooling/heating of a patient. In any case, the amount of cooling or heating provided by such pads 28 may be changed by varying the pressure, flow rate or the temperature of the fluid circulated by the fluid supply pump 14. For example, the control module 12 may be connected to an adjustable valve, which may be opened or closed depending on the desired flow rate of the fluid. Furthermore, the control module 12 may be interconnected to fluid temperature sensors (not shown) and or the heat exchanger 8 to monitor and/or regulate the body cooling system 10.

The PAOH heating system 5 and body cooling system 10 (i.e., the system) disclosed in FIG. 1 have a particular usefulness in providing a treatment for victims of strokes. It has been discovered that the effects of a stroke may be reduced if a mild hypothermia is induced in the victim of the stroke soon after the stroke has incurred. The induction of mild hypothermia has been shown to inhibit several points of the chemical cascade that causes secondary cellular death after an ischemic event and to provide broad neuroprotection. However, it will be noted that the system is not limited to treatment of stroke patients. In this regard, there is evidence that the effects of cardiac arrest as well as head trauma may also be tempered through induced hypothermia. Accordingly, the system disclosed herein may be applied to other medical conditions.

Figure 2:
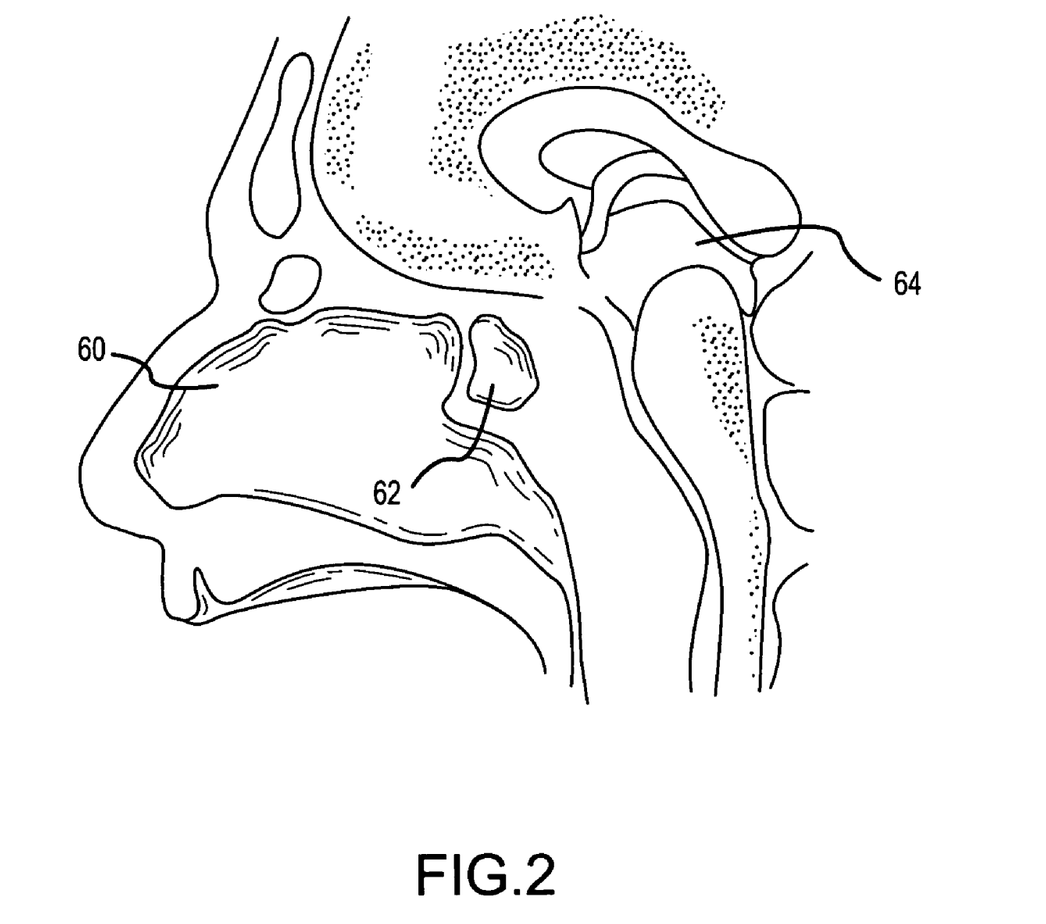
FIG. 2 shows the location of the POAH within a patient skull.

As noted, one method of inducing mild hypothermia in a stroke patient is to provide localized heating of the POAH, which is a thermostat for sensing core body temperature and controlling thermal regulatory responses in mammals. The POAH 64 is located in the lower portion of the brain adjacent to the skull near the nasal cavities 62, 64. See FIG. 2. Local increases in POAH temperature can cause decreases in metabolic heat production (oxygen consumption), vasodilatation enhancing skin cooling, and sweating. Accordingly, varying the temperature of the POAH allows for varying the core body temperature of a patient.

Employing the PAOH heating system 5 described herein, heating of the POAH is performed by directing ultrasound energy at the POAH. In order to achieve this heating, the transducer device 20 may be positioned extracorporeally to a patient's skull and focus ultrasound energy (i.e., sound waves) toward or onto the POAH. In order to focus the transducer device 20 at the POAH, it may be necessary to utilize diagnostic ultrasound or other visualization methods (e.g., MRI) in conjunction with placement of the transducer device 20 relative to the patient's head.

Ultrasound is a mechanical wave with a frequency above the audible range that propagates by the motion of particles so that a pressure wave travels along with a mechanical disturbance. The major advantage of using ultrasound for non-invasive tissue heating is that it penetrates tissue well and can be focused deep into a patient's body to heat a predetermined tissue region (e.g., the POAH). When focused, ultrasound energy emitted by a transducer device 20 (e.g., an ultrasound beam) passes through the patient's skin and tissue over a wide area at intensities that cause little or no heating to intervening tissue and then converge onto the region of focus.

As the ultrasound beams propagate through tissue, part of the energy is absorbed and converted into thermal energy. Typically, the temperature elevation of the tissue caused by the energy absorption is inversely proportional to the ultrasound beam area. However, the greatest temperature elevation is induced at the region of focus, where it can be several orders of magnitude greater than in the overlying tissue. This allows tissue at the region of focus to be selectively heated while minimally elevating the temperature in surrounding tissue (e.g., less than 1° C.). As will be appreciated, this allows for heating of the POAH without substantially heating the overlying tissue.

Typical ultrasound transducer devices produce a beam or sound wave that can be aimed in a specific direction. These sound waves typically obey the laws of geometric optics with regard to reflection, transmission, and refraction and are propagated at a speed of approximately 1,540 meters per second in soft tissue. Portions of such sound waves reflected back to the transducer may be received and displayed on an oscilloscope screen or video monitor. Typically, these transducer devices 20 include a plurality of sound generating elements (e.g. several hundred piezo-electric crystals) for controllably generating ultrasound beams. In this regard, multiple sound generating elements may be arranged to focus multiple ultrasound beams in rapid succession on a common region within a patient's body.

The transducer device 20 of the present embodiment may utilize self-focusing radiators, lenses, reflectors as well as electrically focusing phased arrays to produce a focused ultrasound beam. In any case, the transducer device 20 provides a plurality of ultrasound beams that may each propagate through an individual tissue path to the region of focus. These ultrasound beams will converge in the region of focus, thereby heating the region of focus. As will be appreciated, the region of focus may range in size from a small focal point to a region about the size of an almond.

Figure 3A:
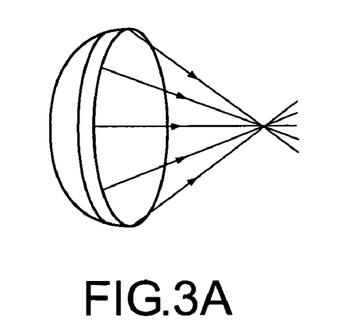
FIGS. 3a–3d show four embodiments of ultrasound transducer focusing systems.
Figure 3B:
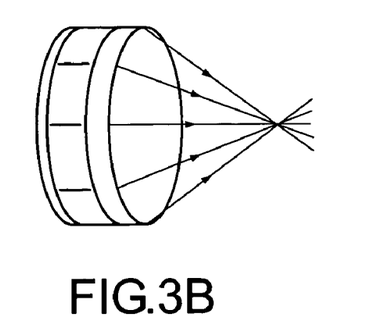
Figure 3C:
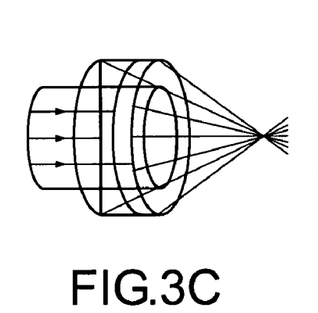
Figure 3D:
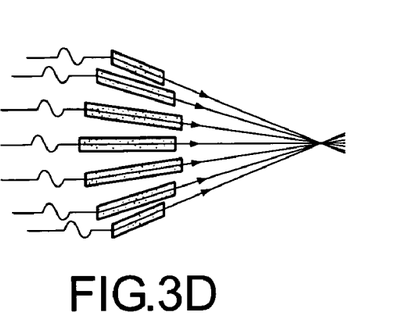

FIGS. 3a–3d show four transducer devices 20 that may be utilized to focus ultrasound beams within a patient's body. FIG. 3a shows a spherical transducer, which is commonly used in medical ultrasound applications, FIG. 3b shows a lens transducer, and FIG. 3c shows a reflective transducer. These transducers variously focus ultrasound beams by interposing a lens or reflector between a flat electric plate containing a plurality of sound generating elements and a target (e.g., region of focus), or, in the case of the spherical transducer, by curving the electric plate. FIG. 3d illustrates an electrical focusing transducer that utilizes a phased array of sound generating elements and coordinated control signals to focus multiple ultrasound beams on a desired region. Electrical focusing allows such transducer devices to simultaneously generate multiple focus spots and may provide for improved control of a resulting ultrasound beam. In this regard, an enhanced region within a patient's tissue may be heated or a region may be more evenly heated.

The transducer device 20, in addition to utilizing any of a variety of focusing systems may also be formed in different shapes and sizes for use in different ultrasound applications. For example, obstetrics scanning transducer devices (i.e. probes) typically resemble a curved soap bar (i.e. a convex array transducer). For other applications, transducer devices may have relatively flat surfaces (i.e., a linear-array transducers). Furthermore, such ultrasound transducer devices may be long and slender to fit within a patient's body for internal ultrasound applications (e.g., vaginal scans). In this regard, the transducer device 20 utilized with the current PAOH heating system 5 may be formed in a manner for conformal positioning relative to the patient's skull, or, for insertion within a nasal/sinus cavity and/or mouth of the patient. Furthermore, the transducer device 20 may be readily removable from the ultrasound module 18 such that a plurality of differently shaped transducer devices 20 may be utilized.

Irrespective of the exact transducer device 20 utilized, ultrasound energy is delivered to at least a portion of the POAH, which may then spread by thermal conduction, so that heating of the entire POAH may occur. Preferably, the entire POAH is evenly heated. As will be appreciated, focused ultrasound allows for non-invasive and controllable heating of the POAH to induce mild hypothermia into a non-sedated patient. However, one drawback of using ultrasound is that bone and gas (e.g., air) interfere with ultrasound beam propagation. Accordingly, heating of the PAOH within the skull can be problematic.

Figure 4:
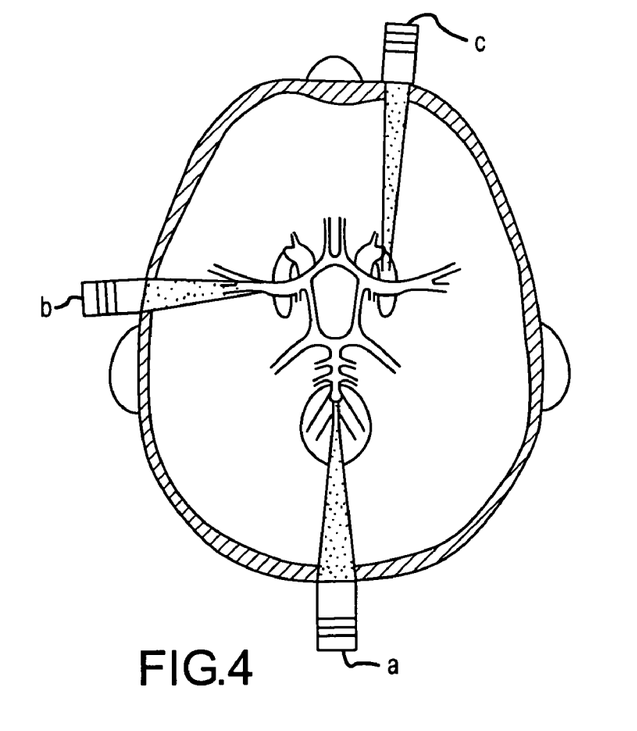
FIG. 4 shows three transcranial windows that may be utilized with the system of FIG. 1.

As a patient's skull will reflect a portion of emitted ultrasound energy, the type and/or positioning of the transducer device 20 must be selected to account for such losses. In this regard, ultrasound may be focused through one or more "transcranial windows" to focus on a tissue region within the skull. Such transcranial windows allow for a sufficient amount of emitted ultrasound energy to be transmitted to the POAH in order to elevate the temperature of the POAH. Transcranial windows may include regions of temporal calvarial thinning within the skull, the orbits of the eye, and the foramen magnum. As shown in FIG. 4, a first transcranial window, the transocipital window (a) provides access from the back of the skull; the transtemporal window (b) allows for access from the side of the skull; and the transorbital window (c) allows access from the front of the skull.

Various forms of medical ultrasound exist for various medical procedures. Different forms of medical ultrasound may be broadly categorized as diagnostic ultrasound, physiotherapy ultrasound, and surgical ultrasound. Diagnostic ultrasound (e.g., TCD) is used primarily for imaging purposes. Physiotherapy ultrasound is often utilized for relieving pain, accelerating wound healing, and reducing swelling. Surgical ultrasound is typically utilized for destruction of patient tissue (e.g. cauterization of tumors). The frequency ranges, power, intensity and pulse length settings generally associated with physiotherapy ultrasound are utilized with the current PAOH heating system 5. However, it will be appreciated that depending on the settings utilized, diagnostic and/or surgical ultrasound devices may also be utilized. In this regard, it is believed that the full medical ultrasound frequency range and power levels may be utilized with the present system 5. In any case, the settings of the transducer device 20 may be set at a first predetermined level for initial POAH heating and those settings (e.g., power, intensity, pulse length and/or frequency) may be subsequently increased or decreased depending on body temperature feedback, as will be discussed herein.

In order to heat the POAH, the transducer device 20 is semi-permanently affixed to the patient's skull using an adhesive and/or headband to maintain proper focus on the POAH. In one embodiment, the transducer device 20 is incorporated into a flexible cap 60 that may be fitted to a patient's head (see FIG. 5). As shown, the cap 60 has first and second temporal ports 70 for receiving first and second transducer devices 20. In this regard, it will be noted that the PAOH heating system 5 may utilize multiple transducer devices 20 for focusing ultrasound on the POAH from different perspectives. That is, beams from separate transducer devices 20 may bisect or triangulate at the POAH for heating purposes. As shown in FIG. 4, the cap 60 is formed from a flexible membrane covering that allows for circulating liquid (e.g., water) over a patient's head. In this regard, the cap 60 also forms a cooling/heating pad 28 for the body cooling system 5. Such a device is disclosed in U.S. Pat. No. 6,461,379, entitled "Localized Bodily Cooling/Heating Apparatus and Method," the content of which is incorporated herein as if set forth in full.

Figure 5:
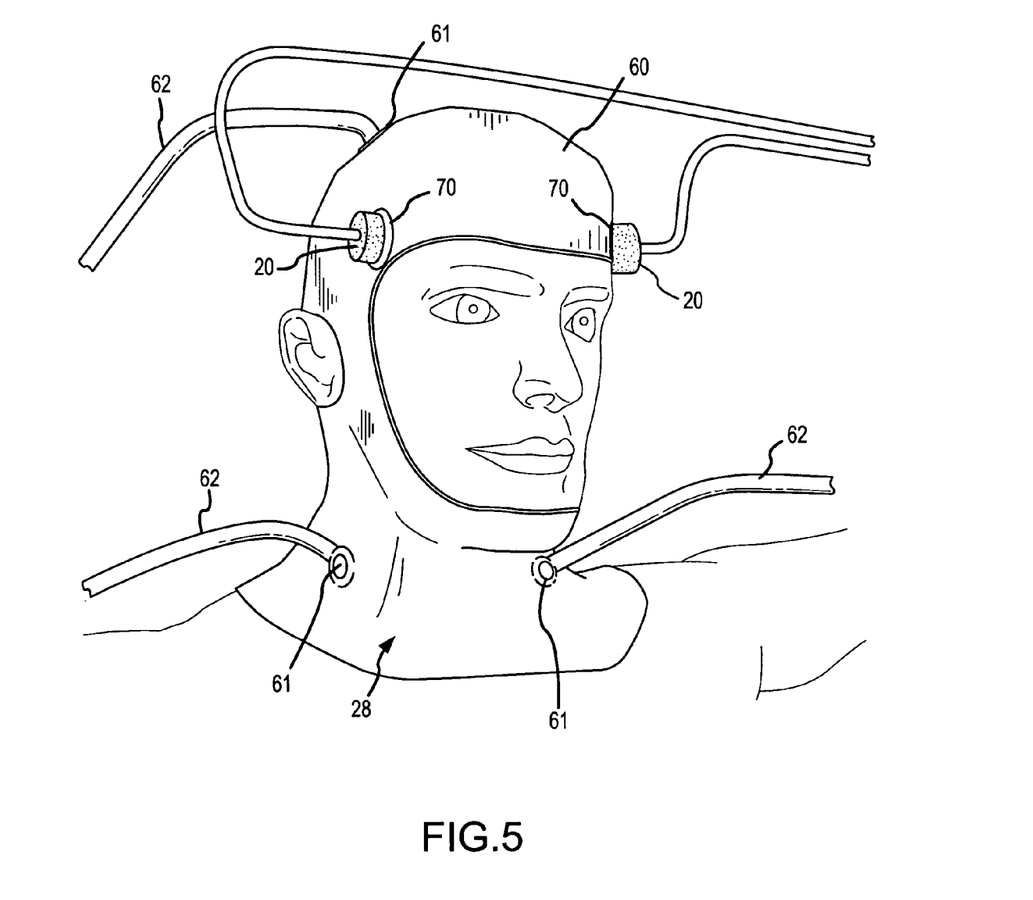
FIG. 5 shows a cooling cap for maintaining a transducer in contact with a patient's skull.

The cap 60 allows a liquid to circulate in a space between the patient's head and an inside surface of the cap 60. In particular, the liquid is circulated between at least two fluid ports 61 (e.g., an inlet port and an outlet port) that are each connected to a conduit 62, which may be interconnected to the fluid pump 14. The cap 60 allows liquid to be in direct contact with the patient's head for increased thermal transfer. To prevent liquid from leaking out of underneath the cap 60, the liquid may be circulated through the cap 60 under negative pressure. That is, the fluid pump 14 may draw liquid through the cap 60 as opposed to pushing liquid through the cap 60.

Figure 6:
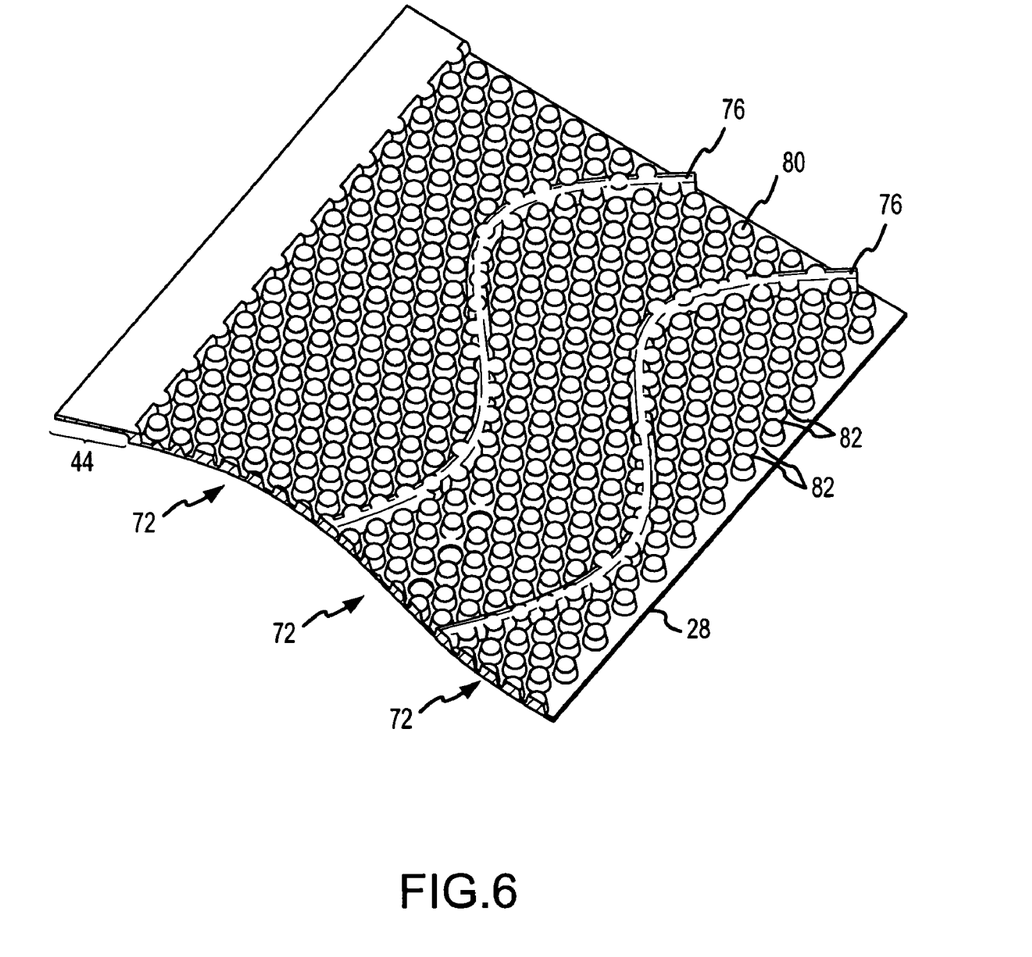
FIG. 6 shows an interior surface of the cap of FIG. 5.

Referring now to FIG. 6, a portion of the interior surface of the cap 60 is shown. To prevent the cap 60 from collapsing during application of negative fluid pressures, the cap 60 includes a spacing structure, which in this embodiment, is comprised of a plurality of ribs 76 and dimples 80. The ribs 76 project from the interior of the flexible membrane of the cap 60 to provide a space or void between the interior of the flexible membrane and the tissue region of interest (e.g., the patient's head) to allow space for the thermal exchange liquid to flow between the various fluid ports 61. The number of ribs 76 used is unimportant, as long as the ribs 76 maintain at least a portion of the interior of the flexible membrane in a spaced relation with the tissue region of interest. As shown, the plurality of ribs 76, the interior of the flexible membrane, and the tissue region of interest will define a plurality of tortuous fluid flow paths 72 between the fluid ports 61. In this regard, the fluid flow paths 72 may be of generally equal length in order to assure consistent fluid velocity across the entire surface of the tissue region of interest. Additionally, the fluid flow paths 72 inhibit the formation of boundary layers of stationary thermal exchange fluid that may reduce the overall efficiency of the cap 60.

In addition to the ribs 76, a plurality of dimples 80 projects from the interior of the flexible membrane. As shown, the dimples 80 are uniformly arrayed in rows and columns on the interior surface of the flexible membrane and define a plurality of interconnecting spaces 82 therebetween. The ribs 76 serpentine across the interior 30 of the flexible membrane 28 and overlap the dimples 80 on occasion. In this illustrated embodiment, the dimples 80 are fashioned in the form of a cylinder, but it will be appreciated that dimples 80 of other than cylindrical shapes may be used. Also, the dimples 80 need not be arrayed in rows and columns. In any case, the interconnecting spaces 82 generally allow water or other thermal exchange liquid to flow therethrough, and further define a tortuous flow path within the fluid flow path 72, which further inhibits the formation of boundary layers. Finally, it will be noted that the cap 60 includes a sealable edge 44 that, under a negative pressure, may conform to a patient's tissue confining liquid within the space beneath the flexible membrane.

Use of a circulating liquid between the transducer device(s) 20 and the patient's skin also allows for enhanced ultrasound coupling. That is, the liquid beneath the cap 60 may form an acoustic coupler, which eliminates air pockets between the transducer device 20 and the patient's skin. However, it will be appreciated, that other acoustic couplers may also be utilized including, without limitation, water based gels, starch, vegetable oils and mineral oils. Furthermore, such acoustic couplers may be utilized with or without the cap 60 shown in FIG. 5.

Figure 7:
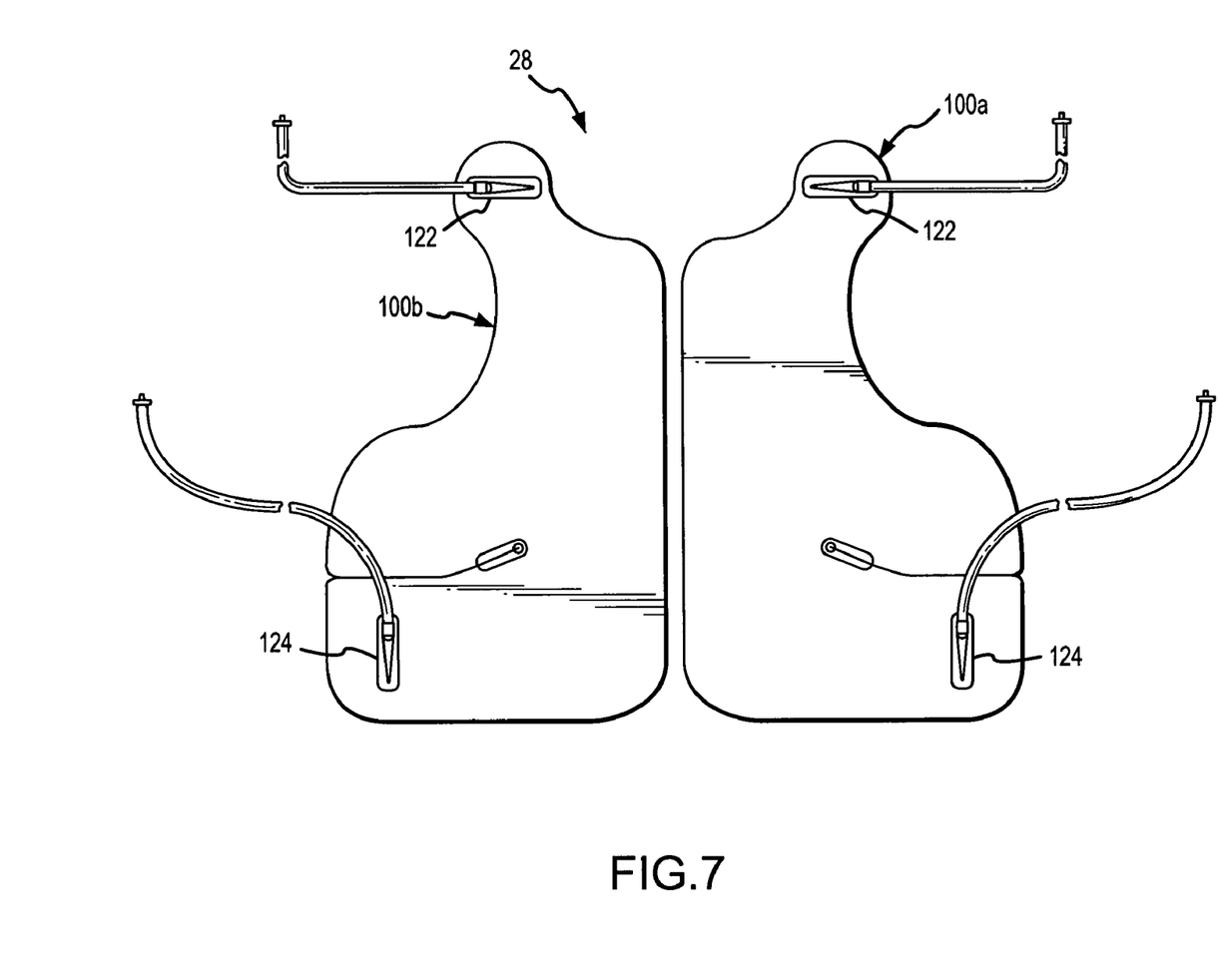
FIG. 7 shows a cooling pad that may be utilized with the system of FIG. 1.
Figure 8:
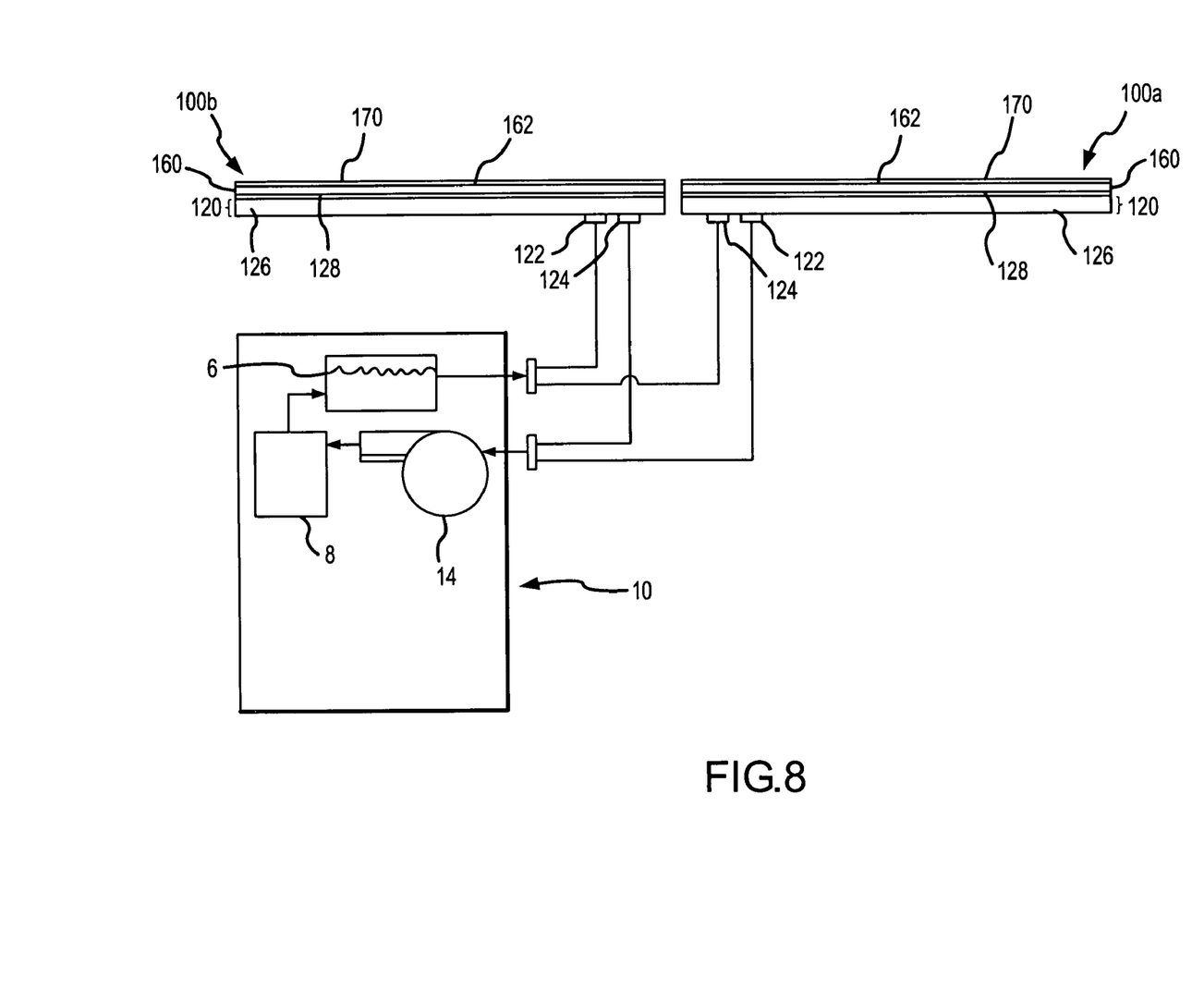
FIG. 8 shows a cross-section view of the layers of the cooling pad of FIG. 7.
Figure 9:
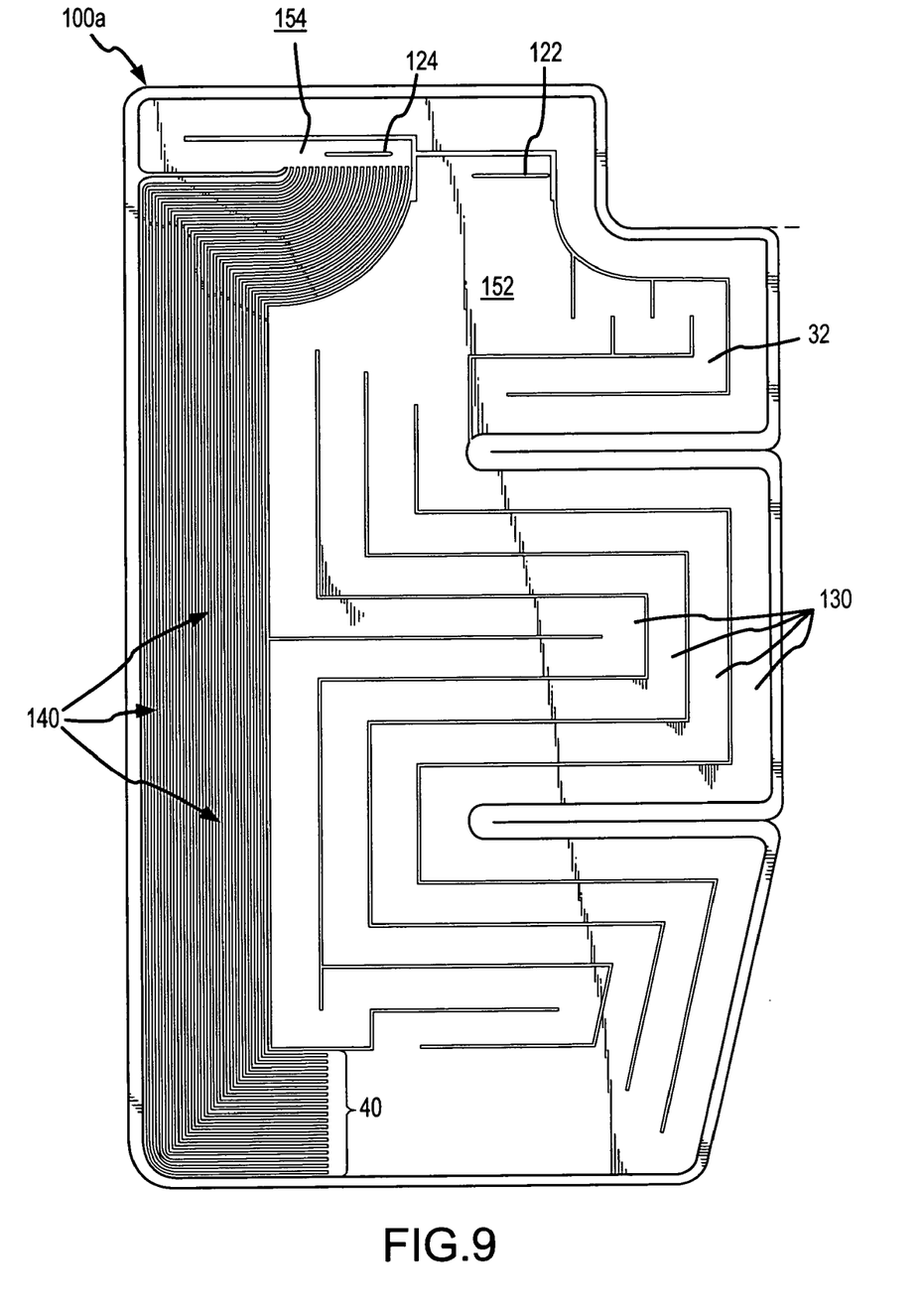
FIG. 9 shows one embodiment of the fluid channels within the cooling pad of FIG. 7.

In addition to, or in place of the cooling cap 60, the present invention may further utilize other cooling/heating pads, which are operative to cool/heat other portions of a patient's body for temperature regulation purposes. That is, one or more cooling/heating pads 28 may be interconnected to the fluid pump 14 and placed in contact with a patient's body to exchange thermal energy. For example, FIGS. 7–9 illustrate a coolant pad 28 that is adapted to fit on a patient's back. As shown in FIG. 7, the coolant pad 28 comprises two matching pads 100a and 100b formed into a jacket that may be applied to a patient's torso. Referring now to the schematic illustration of FIG. 8, another embodiment of a body cooling system 10 utilizing the back pads 100a and 100b is shown.

The illustrated back pads 100a and 100b each include fluid containing layers 120 through which fluid may be circulated during use. That is, fluid may be circulated through fluid ports 122, 124 of the fluid containing layers 120, respectively by the interconnectable fluid pump 14. In the arrangement shown the pump 14 draws fluid through the back pads 100a and 100b under negative pressure (e.g. less than about −10 psi). This fluid then passes though at least one heat exchanger 8 to heat and/or cool the fluid, and a fluid reservoir 6.

In addition to a fluid-containing layer 120, the back pads 100 may each further include a conformable, thermally conductive layer 160 for contacting the skin of a patient. In this regard, the conformable layer 160 may provide an adhesive surface 162 for enhancing the pad-to-skin interface. Preferably, the adhesive surface 162 extends across a major portion (e.g. substantially all) of the pads 100a, 100b. A release liner 170 may also be provided on the adhesive surface 162 for removal prior to use.

Each of the fluid containing layers 120 may comprise opposing first and second layers 126, 128, respectively, with a number of fluid channels defined by a plurality of rib members therewithin. As shown by FIG. 9, the fluid containing layer 120 may include rib members that define a first plurality of adjacent fluid channels 130 and a second plurality of adjacent fluid channels 140 extending between the fluid ports 122, 124 of the pads 100. As may be appreciated, fluid may be circulated from port 122 to port 124, or alternately from port 124 to port 122.

In the illustrated embodiments, the first plurality of channels 130 are of coincidental, serpentine configuration. More particularly, each of the channels comprising the first plurality of channels 130 is of an S-shaped configuration. Further, such channels 130 may be of a substantially common length. These channels 130 may also have a substantially common average width.

The second plurality of channels 140 is also disposed in a coincidental manner. As illustrated, a major portion of each of the channels comprising the second plurality of channels 140 follows a substantially linear path. Further, it should be noted that channels 140 may be of a substantially common length, and width.

Fluid staging chambers 152 and 154 are provided at the fluid ports 122 and 154, respectively. Such staging chambers serve to distribute fluid and normalize fluid flow through the first plurality of channels 130 and second plurality of channels 140.

It will be appreciated that the internal structure of the back pads 100a and 100b may be varied. For example, each pad may have only a single set of channels and/or utilize a matrix of dimples (e.g., see FIG. 6) to prevent the channels from collapsing under negative pressure. Furthermore, external pads designed for use on other portions of the body may be utilized as well (e.g., on the thigh, arms and/or neck). In any case, use of external cooling pads 28 may be synchronized with ultrasound heating of the PAOH to increase the rate of core body temperature reduction. Likewise, such pads 28 may be utilized to provide heat in order to raise a patient's core body temperature (e.g., after maintaining mild hypothermia for a predetermined period). Such cooling/heating pads are disclosed in U.S. Pat. No. 6,375,674, entitled "Cooling/Heating Pad and System", the contents of which are incorporated herein as if set forth in full.

Figure 10:
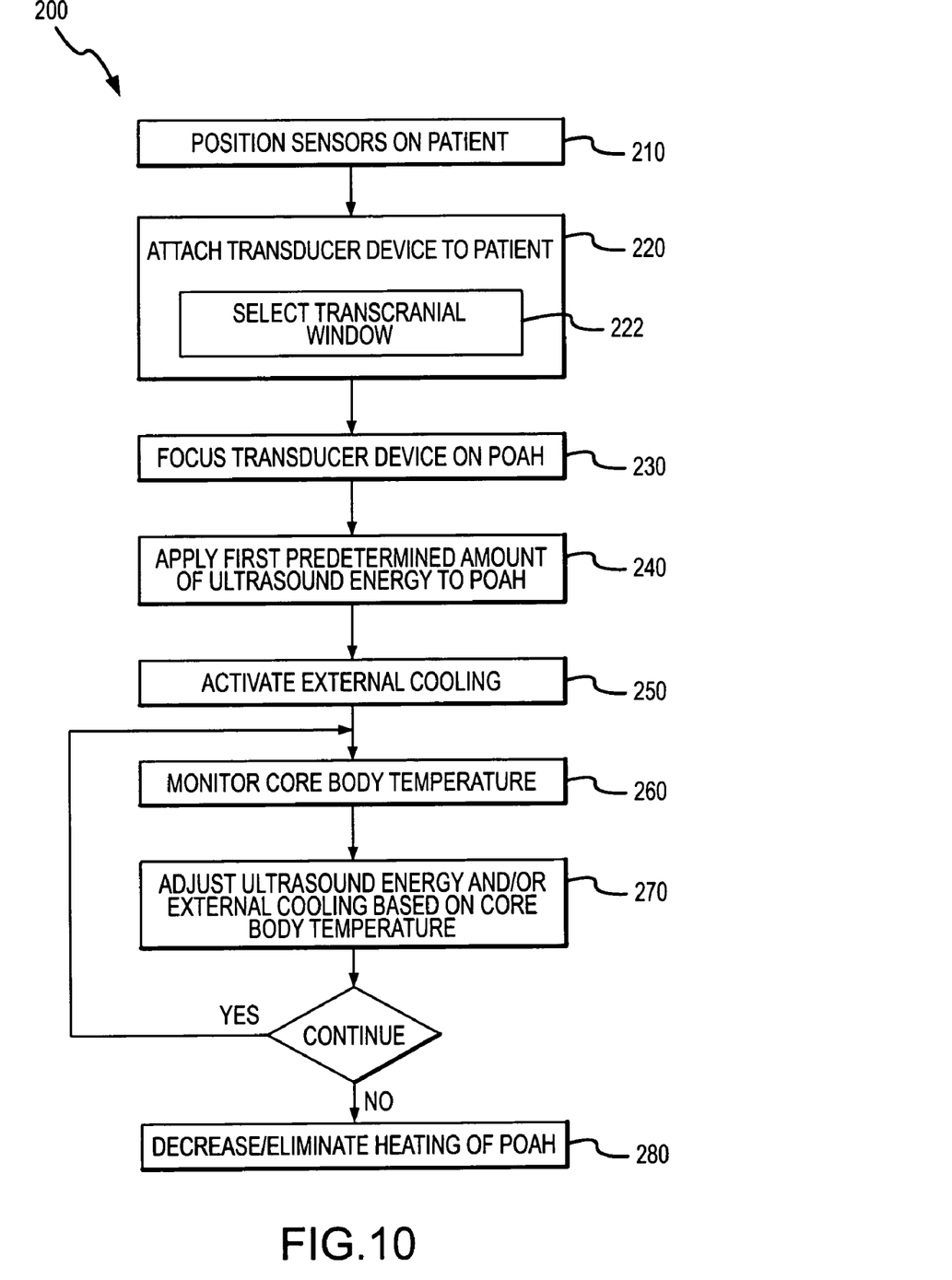
FIG. 10 shows a process flow chart of a heating process that may be performed by the system of FIG. 1.

FIG. 10 shows a process flowchart of an exemplary process 200 that may be performed by the PAOH heating system 5 described above. In operation, prior to the emission of any ultrasound energy to heat the POAH, the temperature sensor(s) is positioned (210) on the patient. For example, a skin conductivity sensor 24 may be attached to any exterior skin surface of the patient, however to provide an optimal reading, the electrodes may be positioned somewhere about the head region. A core body temperature sensor 22 may be placed on any bodily region that would provide an accurate indication of the core body temperature. These portions of the body include the tympanic membrane, esophageal or the nasopharyngeal.

At this point, the transducer device 20 may be attached (220) to the patient's body. In positioning the transducer device 20 it is desirable to find a location that provides ready access to the POAH while minimizing the amount of intervening bone tissue. In this regard, the step of attaching (220) may further include selecting (222) an appropriate transcranial window. Once the transducer device 20 is positioned relative to a selected transcranial window, the transducer device 20 may be focused (230) on the POAH.

One initial procedure for focusing (230) ultrasound energy to the POAH, includes locating an optimal position for the transducer device 20. This may be done by a clinician through use of the skin conductivity sensor. While locating this optimal position, a low power ultrasound signal may be emitted from the transducer device 20. The clinician then moves the transducer device 20 to different orientations relative to the selected transcranial window. Based on the heating provided, the POAH will initiate thermoregulatory cooling processes that include sweating. The skin conductivity will change as a result of the hypothalamus sensing a minor, 0.25–0.5° Celsius increase in core temperature and initiate sweating as a primary response to the sensed core temperature rise. The optimal position for the transducer device 20 corresponds with the maximum conductivity detected by the sensors.

Once the transducer device 20 has been optimally focused (230), the energy provided to the transducer device 20 may be increased (240) to a first predetermined setting to affect a desired increase in POAH temperature (e.g., 0.5–4° Celsius). The body's natural reaction to the POAH warming will be to reduce metabolic heat generation, vasodilatate, and generate sweat. At this time, the core body temperature will begin to drop.

Prior to the emission of ultrasound energy or simultaneously therewith, a body cooling system 10 may be activated (250). The body cooling system 10, through the circulation of a thermal exchange liquid through one or more coolant pads 28, may provide external cooling to contacted bodily tissues of the patient. The cooling applied to the tissue by the body cooling system 10 may be based on the temperature of the thermal exchange liquid, the rate of circulation, and/or a current core body temperature.

The drop in core temperature will be monitored (260) by the core temperature sensors and temperature signals will be fed back to the control module 12. The body's cooling process will also act to cool the POAH. As the core temperature sensor 22 feeds back a signal to the control module 12 that the temperature has dropped, the energy to the transducer device 20 and/or the body cooling system 10 may be adjusted (270) proportionately, to maintain the POAH temperature above the physiologic set point. The absolute temperature of the POAH may not rise (due to the body's cooling effects being offset by the increased application of ultrasound) but the differential temperature between the POAH and surrounding tissue would increase. One advantage of the POAH heating system described herein is that through use of the cooling apparatus, heating the POAH may be achieved with little or no heating of the tissues that surround the POAH. That is, the focused ultrasound energy results in a net rise in temperature within an isolated region (i.e., POAH) deep within the brain tissue while allowing the global temperature of the brain to be reduced.

Once the desired temperature decrease has been achieved for the desired period of time, the energy provided to the transducer device 20 may then be decreased (280) at a selected rate to achieve a controlled increase in core temperature back to normal body temperature. Once the rise in temperature is complete, the transducer device 20 and sensors may be removed from the patient.

The foregoing description of the present invention has been presented for purposes of illustration and description. Furthermore, the description is not intended to limit the invention to the form disclosed herein. It is intended that the appended claims be construed to include alternative embodiments to the extent permitted by the prior art.

The invention claimed is:

1. A method for inducing mild hypothermia in a patient body, comprising:
    positioning a source of ultrasound energy relative to a patient skull;
    applying ultrasound energy to a tissue region that at least partially coincides with a preoptic anterior hypothalamus (POAH) region in the patient skull to affect thermoregulatory responses of the body;
    providing artificial cooling to a portion of the patient body to reduce a core temperature of the body.

2. The method of claim 1, wherein said step of applying is performed extracorporeally.

3. The method of claim 1, wherein said step of applying comprises applying a predetermined amount of ultrasound energy in order to increase the temperature of the POAH between about 0.5° C. and about 4° C.

4. The method of claim 1, wherein said step of providing artificial cooling comprises providing intracorporeal cooling.

5. The method of claim 4, wherein said step of providing intracorporeal cooling comprises one of:
   endovascular cooling; and
   cooling of the peritoneum.

6. The method of claim 1, wherein said step of providing artificial cooling comprises cooling an external surface of said body.

7. The method of claim 6, wherein said cooling is provided using a contact cooling means.

8. The method of claim 7, wherein said contact cooling means circulates a thermal exchange fluid relative to a tissue region of said patient body to provide said cooling.

9. The method of claim 8, wherein said thermal exchange fluid directly contacts patient tissue to provide said cooling.

10. The method of claim 8, wherein said thermal exchange fluid circulates through a contact pad to conduct thermal energy away from said tissue region.

11. The method of claim 10, wherein said thermal exchange fluid circulates through at least one channel formed by a least one rib in an internal structure of said pad.

12. The method of claim 10, wherein said contact pad is adhered to said body.

13. The method of claim 12, wherein said contact pad is adhered using a thermally conductive hydrogel.

14. The method of claim 8, wherein said thermal exchange fluid circulates under a negative pressure.

15. The method of claim 6, wherein said cooling is localized to the head of the patient.

16. A method for providing localized heating to the preoptic anterior hypothalamus (POAH) of a body to induce mild hypothermia in that body comprising:
   positioning a source of ultrasound energy relative to a patient skull;
   focusing said source of ultrasound energy on a tissue region within the patient skull, wherein said tissue region at least partially encompasses the preoptic anterior hypothalamus (POAH) of a body; and
   applying a predetermined amount of ultrasound energy to said tissue region, wherein said ultrasound increases the temperature of said tissue region to heat the POAH.

17. The method of claim 16, wherein said step of applying comprises applying a predetermined amount of ultrasound energy to increase the temperature of said tissue region between about 0.5° C. and about 4° C.

18. The method of claim 17, wherein, for a given tissue type in said tissue region, said tissue is heated evenly.

19. The method of claim 16, wherein applying comprises applying ultrasound energy having a power between about 0.05 W and about 100 W.

20. The method of claim 16, wherein applying comprises applying ultrasound energy having an intensity between about 2.0 W/cm$^2$ and about 100 W/cm$^2$.

21. The method of claim 16, wherein applying comprises applying ultrasound energy having a frequency between about 0.5 MHz and about 10 MHz.

22. The method of claim 16, further comprising:
   providing cooling to at least a portion of the patient's body.

23. The method of claim 22, wherein said cooling is provided to an external portion of the patient'body.

24. The method of claim 23, wherein said cooling is provided via direct surface contact.

25. The method of claim 24, wherein said cooling is localized to a patient's head.

26. The method of claim 16, wherein said step of positioning comprises positioning said source extracorporeally to the patient skull.

27. The method of claim 26, wherein said source is positioned relative to a transcranial window such that ultrasound may pass into the patient skull.

28. The method of claim 27, wherein said transcranial window is selected from a group consisting of:
   a transocipitl window;
   a transtemporal window; and
   a transorbital window.

29. The method of claim 16, wherein said step of focusing further comprises:
   identifying said tissue region utilizing a diagnostic visualization procedure.

30. The method of claim 29, wherein said diagnostic visualization procedure comprises at least one of diagnostic ultrasound or MRI.

31. The method of claim 16, further comprising monitoring at least one of:
   a core body temperature sensor operative to provide a signal indicative of the core body temperature of a patient body; and
   a skin conductivity sensor operative to provide a signal indicative of skin conductivity.

32. The method of claim 31, wherein said predetermined amount of ultrasound energy is adjusted based on at least one of said signals.

33. A system for providing localized heating to the preoptic anterior hypothalamus (POAH) of a body to induce mild hypothermia in that body comprising:
   a source of ultrasound energy operative to focus ultrasound energy on a tissue region within a patient skull, wherein the tissue region at least partially encompasses said POAH;
   at least one sensor positionable at a predetermined location on the body which provides feedback signals indicative of a temperature of the body, wherein said at least one sensor includes at least one of:
   a core body temperature sensor positionable at a first predetermined location on the body which provides a first feedback signal indicative of the core temperature of the body; and
   a skin conductivity sensor positionable at a second predetermined location on the body which provides a second feedback signal indicative of skin conductivity; and
   a controller connectable to the at least one sensor which controls power to the source of ultrasound energy in an amount proportional to the magnitude of the feedback signal received from the at least one sensor.

34. The system of claim 33, further including a cooling system for providing artificial cooling to at least a first portion of the body.

35. The system of claim 34 wherein the cooling system comprises a membrane through which a thermal exchange fluid may be circulated.

36. The system of claim 35, wherein the membrane is adapted to provide surface contact cooling.

37. The system of claim 36, wherein said membrane includes internal structure to allow said thermal exchange fluid to be circulated under negative pressure.

38. The system of claim 35 wherein said membrane is adapted to allow the direct coolant contact a portion of the body.

39. The system of claim 38, wherein said membrane is adapted to be positioned on the head of a patient.

40. The system of claim 35, wherein said cooling system further includes:
  a pumping device;
  a fluid reservoir; and
  a heat exchanger for controlling the temperature of the thermal exchange fluid.

41. The system of claim 33, wherein said source comprises an ultrasound transducer.

42. The system of claim 41, wherein said ultrasound transducer is selected from a group of focusing transducers consisting of:
  spherical transducers;
  lens transducers;
  reflective transducers; and
  electrically focusing transducers.

43. The system of claim 33, wherein the core body temperature sensor is attachable to at least one of: tympanic membrane, esophageal, and nasopharyngeal.

44. The system of claim 33, wherein the skin conductivity sensor comprises at least two electrodes attachable to an exterior skin surface of the body, across which the conductivity of bodily fluids emitted by the body are measurable.

* * * * *